United States Patent
Bordignon et al.

(12) 
(10) Patent No.: US 6,268,214 B1
(45) Date of Patent: *Jul. 31, 2001

(54) VECTORS ENCODING A MODIFIED LOW AFFINITY NERVE GROWTH FACTOR RECEPTOR

(75) Inventors: Claudio Bordignon; Fulvio Mavilio, both of Milan (IT)

(73) Assignee: Roche Diagnostics GmbH, Mannheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/094,577

(22) Filed: Jun. 12, 1998

Related U.S. Application Data (63) Continuation-in-part of application No. 08/737,343, filed on Jan. 13, 1997, now abandoned, and a continuation-in-part of application No. 08/602,791, filed on Apr. 4, 1996, now Pat. No. 6,074,836.

(51) Int. Cl.[7] ............................ C12N 15/63; C12N 15/85; A61K 35/00
(52) U.S. Cl. ...................... 435/320.1; 435/324; 435/375; 435/335; 435/343; 435/343.1; 435/343.2; 424/93.21; 424/93.2
(58) Field of Search ............................... 424/93.21, 93.2; 435/320.1, 325, 375, 335, 343, 343.1, 343.2

(56) References Cited

U.S. PATENT DOCUMENTS

| | | | |
|---|---|---|---|
| 5,055,459 | 10/1991 | Andersson et al. | 514/114 |
| 5,470,730 | 11/1995 | Greenberg et al. | 435/172.3 |

FOREIGN PATENT DOCUMENTS

| | | |
|---|---|---|
| 0 455 460 A2 | 11/1991 | (EP) . |
| WO 91/16069 | 10/1991 | (WO) . |
| WO 92/01810 | 2/1992 | (WO) . |
| WO 92/05262 | 4/1992 | (WO) . |
| WO 92/08796 | 5/1992 | (WO) . |
| WO 92/09631 | 6/1992 | (WO) . |
| WO 92/19749 | 11/1992 | (WO) . |
| WO 93/04167 | 3/1993 | (WO) . |

OTHER PUBLICATIONS

Areman et al., Bone Marrow Transplant, vol. 18, No. 3, pp. 521–525 (1996), "Hematopoietic potential of IL–2–cultured peripheral blood stem cells from breast cancer patients".

Areman et al., Transfus. Med. Rev., vol. 5, No. 3, pp. 214–227 (1991), "Bone marrow processing for transplantation".

Areman et al., Transfusion, vol. 31, No. 8, pp. 724–730 (1991), "Automated processing of human bone marrow can result in a population of mononuclear cells capable of achieving engraftment following transplantation".

Juneja et al., Leukemia, vol. 9, No. 10, pp. 1771–1778 (1995), "Successful in vitro purging of leukemic blasts from marrow by cortivazol, a pyrazolosteroid: a preclinical study for autologous transplantation in acute lymphoblastic leukemia and non–Hodgkin's lymphoma".

Negrin et al., Blood, vol. 85, No. 11, pp. 3334–3341 (1995), "Transplantation of enriched and purged peripheral blood progenitor cells from a single apheresis product in patients with non–Hodgkin's lymphoma".

Rubin et al., J. Hematother. vol. 3, No. 2, pp. 121–127 (1994, "A combination of anti–CD15 monoclonal antibody PM–81 and 4–hydroperoxycyclophosphamide augments tumor cytotoxicity while sparing normal progenitor cells".

Soiffer et al., Bone Marrow Transplant, vol. 12, No. 3, p. 243–251 (1993), "Monoclonal antibody–purged autologous bone marrow transplantation in adults with acute lymphoblastic leukemia at high risk of relapse".

Volger et al., J. Hematother., vol. 2, No. 1, pp. 93–102 (1993), "Autologous bone marro w transplantation with alkyl–lysophospholipid–purged marrow".

Gribben et al., Leuk. Lymphoma, vol. 11, Suppl. 2, pp. 141–148 (1993), "Bone marrow purging for autologous bone marrow transplantation".

Stiff et al., Blood, vol. 77, No. 2, pp. 355–362 (1991), "Anti–CD33 monoclonal antibody and etoposide/cytosine arabinoside combinations for the ex vivo purification of bone marrow in acute nonlymphocytic leukemia".

Prejers et al., Br. J. Haematol., vol. 71, No. 2, pp. 195–201 (1989), "Cytotoxic potential of anti–CD7 immunotoxin (WT1–ricin A) to purge ex vivo malignant T cells in bone marrow immunological monitoring".

Heslop et al., Human Gene Therapy, vol. 5, No. 3, pp. 381–397 (1994), "Administration of neomycin resistance gene marked EBV specific cytotoxic T lymphocytes to recipients of mismatched–related or phenotypically similar unrelated donor marrow grafts".

Freeman et al., J. Cell. Biochem., Keystone Symposia on Molecular and Cellular Biology, Suppl. 16F, p. 47, V209, Apr. 3–16, 1992, "Tumor regression when a fraction of the tumor mass contains the HSV–TK gene".

(List continued on next page.)

Primary Examiner—Karen M. Hauda
Assistant Examiner—Anne Marie S Beckerleg
(74) Attorney, Agent, or Firm—Arent Fox Kintner Plotkin & Kahn PLLC (57) ABSTRACT

In the course of therapy following an allogeneic bone marrow transplant (allo-BMT) in which lymphocytes were removed from the transplant, donor lymphocytes are introduced after a delay to reconstitute immunity in the patient. According to the invention, these donor lymphocytes are transduced with a detectable cell surface marker and a suicide gene prior to introducing them into the patient. Introduction of these transduced lymphocytes after allo-BMT, serves to treat or prevent complications from the BMT, including disease relapse, reactivation of viral infection and Graft versus Host disease.

6 Claims, 4 Drawing Sheets

OTHER PUBLICATIONS

Sikora, K., Trends in Biotechnology, vol. 11, No. 5, pp. 197–201 (1993), "gene therapy for cancer".

Caruso et al., Proc. Natl. Acad. Sci. USA, vol. 89, pp.182–186 (1992) "Selective killing of CD4+ cells harboring a human immunodeficiency virus–inducible suicide gene prevents viral spread in an infected cell population".

Pardoll et al., Bone Marrow Transplantation, vol. 9, Suppl. 1, pp. 182–186 (1992), "Molecular engineering of the anti-tumor immune response".

Hérin et al., Intl. J. Cancer, vol. 39, No. 3, pp. 390–396 (1987), "Production of stable cytolytic T–cell clones directed against autologous human melanoma".

Gavioli et al., J. Virology, vol. 673, No. 3, pp. 1572–1578 (1993), "Multiple HLA A11–restricted cytotoxic T–lymphocyte epitopes of different immunogenecities in the Epstein–Barr virus–encoded nuclear antigen 4".

Murray et al., J. Exp. Med., vol. 176, pp. 157–168 (1992), "Identification of target antigens for the human cytotoxic T cell response to Epstein–Barr virus (EBV): Implications for the immune control of EBV–positive malignancies".

Khanna et al., J. Exp. Med., vol. 176, pp. 169–176 (1992), "Localization of Epstein–Barr virus cytotoxic T cell epitopes using recombinant vaccinia: Implications for vaccine development".

Kabelitz et al., J. Mol. Cell Immunol., vol. 3, pp. 49–60 (1987), "Human cytotoxic T lymphocytes. III. Large numbers of peripheral blood T cells clonally develop into allorestricted anti-viral cytotoxic T cell populations in vitro".

Nagler–Anderson et al., Immunological Reviews, No. 103, pp. 111–125 (1988), "A comparison of the cytolytic properties of murine primary CD8+ cytotoxic T lymphocytes and cloned cytotoxic T cell lines".

Carmichael et al., J. Exp. Med., vol. 177, No. 2, pp. 249–256 (1993), "Quantitative analysis of the human immunodeficiency virus type 1 (HIV–1)–specific cytotoxic T lymphocyte (CTL) response at different stages of HIV–1 infection: Differential CTL responses to HIV–1 and Epstein–Barr virus in late disease".

Bachmann et al., Current Opinion in Immunology, vol. 6, No. 2, pp. 320–326 (1994), "In-vivo versus in vitro assays for assessment of T– and B–cell function".

Cullis et al., Blood, vol. 79, pp. 1379–1380 (1992), "Donor leukocyte infusions for chronic myeloid leukemia in relapse after allogenic bone marrow transplantation".

Kolb et al., Blood, vol. 76, No. 12, pp. 2462–2465 (1990), "Donor leukocyte transfusions for treatment of recurrent chronic myelogenous leukemia in marrow transplant patients".

Rybak et al., Derwent Accession No. 93–067423, "Cytotoxic reagents that selectively kill cells e.g. T–cells—consists of mammalian protein as toxic moiety, recognition moiety binding specific cellular surface marker and liner for both moieties".

Riddell et al., Science, vol. 257, pp. 238–241 (1992), "Restoration of viral immunity in immunodeficient humans by the adoptive transfer of T cell clones".

Wickelgren, Science, vol. 276, p. 1646 (1997), "New lead to safer marrow transplants".

Bonini et al., Science, vol. 276, pp. 1719–1724 (1997), "HSV–TK gene transfer into donor lymphocytes for control of allogeneic graft–versus–leukemia".

Rowley et al., Bone marrow and stem cell processing: A manual of current techniques, F.A. Davies Co., Philadelphia: 218–291 (1992).

Bonini et al., Blood, vol. 84, No. 10, Suppl. 1 (427), p. 110a (1994), "Transfer of the HSV–TK gene into donor peripheral blood lymphocytes for in vivo immunomodulation of donor anti–tumor immunity after allo–BMT".

Bordignon et al., Human Gene Therapy, vol. 6, pp. 813–819 (1995), "Transfer of the HSV–tk gene into donor peripheral blood lymphocytes for in vivo modulation of donor anti–tumor immunity after allogeneic bone marrow transplantation".

Gillio et al., Annals New York Academy of Sciences, vol. 551, pp. 406–417 (1987), "Retroviral vector–mediated gene transfer and expression in nonhuman primates following autologous bone marrow transplantation".

Keller et al., Nature, vol. 318, pp. 149–154 (1985), "Expression of a foreign gene in myeloid and lymphoid cells derived from multipotent haematopoietic precursors".

Servida et al., Blood, vol. 82, No. 10, Suppl. 1 (843), p. 214a (1993), "Gene transfer into peripheral blood lymphocytes for in vivo immunomodulation of donor anti–tumor immunity in a patient affected by EBV–induced lymphoma".

Chevalier et al., Blood, vol. 83, No. 6, pp. 1479–1485 (1994), "Expression and functionality of the trkA proto–oncogene product/NGF receptor in undifferentiated hematopoietic cells".

Mavilio et al., Blood, vol. 83, No. 7, pp. 1988–1997 (1994), "Peripheral blood lymphocytes as target cells of retroviral vector–mediated gene transfer".

Reddy et al., Molecular Brain Research, vol. 8, No. 2, pp. 137–141 (1990), "Transient expression of full–length and truncated forms of the human nerve growth factor receptor".

Radeke et al., Nature, vol. 325, pp. 593–597 (1987), "Gene transfer and molecular cloning of the rat nerve growth factor receptor".

Johnson et al., Cell, vol. 47, pp. 545–554 (1986), "Expression and structure of the human NGF receptor".

Wysocki et al., Cell and Developmental Biology, vol. 75, No. 6, pp. 2844–2848 (1978), "'Panning' for lymphocytes: A method for cell selection".

Hempstead et al., J. Biol. Chem., vol. 265, No. 17, pp. 9595–9590 (1990), "Deletion of Cytoplasmic Sequences of the Nerve Growth Factor Receptor Leads to Loss of High Affinity Ligand Binding".

Maryanski et al., J. Immunological Methods, vol. 79, pp. 159–165 (1985), "A simple panning method for the selection of cell surface antigen transfectants".

Fakhrai et al., J. Cell. Biochem., Keystone Symposia on Molecular and Cellular Biology, Suppl. 16F, p. 47, V208, Apr. 3–16, 1992, "Cytokine gene therapy of cancer using transduced fibroblasts".

Traversari et al., Immunogenetics, vol. 35, pp. 145–152 (1992), "Transfection and expression of a gene coding for a human melanoma antigen recognized by autologous cytolytic T lymphocytes".

Helg et al., Bone Marrow Transplantation, vol. 12, pp. 125–129 (1993), "Adoptive immunotherapy for recurrent CML after BMT".

Bär et al., J. Clin. Oncology, vol. 11, No. 3, pp. 513–519 (1993), "Donor leukocyte infusions for chronic myeloid leukemia relapsed after allogenic bone marrow transplantation".

Klingemann et al., Bone Marrow Transplantation, vol. 8, pp. 73–81 (1991), "Immunotherapy after bone marrow transplantation".

Van der Bruggen et al., Science, vol. 254, pp. 1643–1647 (1991), "A gene encoding an antigen recognized by cytolytic T lymphocytes on a human melanoma".

Traversari et al., Gene Therapy, DZ 318, p. 240, "Gene transfer into peripheral blood lymphocytes for in vivo immunomodulation of donor anti–tumor immunity in a patient affected by EBV–induced lymphoma" (1994).

VECTORS ENCODING A MODIFIED LOW AFFINITY NERVE GROWTH FACTOR RECEPTOR

CROSS REFERENCE TO RELATED APPLICATIONS

The present application is a CIP of U.S. application Ser. No. 08/737,343, now abandoned, having an International filing date of May 16, 1994, and a U.S. filing date of Jan. 13, 1997, and a CIP of U.S. application Ser. No. 08/602,791, having an International Filing Date of Aug. 11, 1994, and a U.S. filing date of Apr. 4, 1996, now U.S. Pat. No. 6,074,836. These applications all are incorporated by reference in their entireties herein.

BACKGROUND OF THE INVENTION

Bone marrow transplant represents hope for survival for many patients who suffer from blood, lymphatic and bone-related disorders, and from depleted marrow cells resulting from intensive chemo- and/or radiotherapy. In an "allogeneic" bone marrow transplantation ("allo-BMT"), bone marrow is transplanted from a donor other than the patient (autologous transplant) or the patient's identical sibling (syngeneic transplant).

Allogeneic BMT is the treatment of choice for many hematologic malignancies, such as leukemia, lymphoma and multiple myolema (1, 2). It is the only curative therapy for chronic myeloid leukemia. Transplantation of allogeneic bone marrow, particularly when employed together with high-dose chemoradiotherapy, has been shown to produce superior results compared to autologous or syngeneic transplants (3).

The advantages associated with allogeneic BMT are limited by the risk of a potentially life-threatening complication, graft versus host disease (GvHD). In performing allogeneic BMT, the patient initially undergoes an immunosuppressive regimen to minimize rejection of the graft. Severe GvHD following allo-BMT can be controlled by: (i) treating the patient to eliminate residual recipient alloreactive T cells, and (ii) treating the graft to remove mature alloreactive T lymphocytes (2).

Removal of alloreactive mature T lymphocytes from the allo-BMT increases the incidence of disease relapse, graft rejection and reactivation of viral infection (4). To counteract these effects, allo-BMT patients have been treated by introducing donor T lymphocytes after a delay following allo-BMT.

Recent studies have shown that delayed introduction of donor T lymphocytes following allo-BMT is a promising therapy for reconstituting immunity and treating relapse of several disease states, and a therapy which could render allo-BMT more efficacious. Patients that underwent treatment with allo-BMT devoid of T lymphocytes, when affected by recurrence of chronic myelogenous leukemia, acute leukemia, lymphoma, and multiple myeloma, could achieve complete remission after the infusion of donor leukocytes, without requiring cytoreductive chemotherapy or radiotherapy (5). In other studies, delayed lymphocyte introduction was used to treat complications related to the severe immunosuppression associated with allo-BMT, such as Epstein-Barr virus-induced B lymphoproliferative disorders (EBV-BLPD) (6, 7) and reactivation of cytomegalovirus (CMV) infection (8).

The therapeutic promise of delayed introduction of donor T lymphocytes following allo-BMT, however, remains limited by GvHD, a frequent and potentially lethal complication of the treatment. Currently, no specific treatment exists for established GvHD. Thus, the threat of GvHD must be weighed heavily against the therapeutic effect of allo-BMT, and limits the applications in which the therapy is employed. (9). Accordingly, a regimen for preventing and for treating GvHD is highly desired in order to permit the beneficial use of delayed introduction of donor T lymphocytes following allo-BMT.

In this delayed lymphocyte introduction therapy, there also is a need for a simple method of monitoring the lymphocytes post-infusion. Effective monitoring would permit an investigator to determine whether the infused lymphocytes contribute to or cause a variety of complications which may occur after infusion. Since complications post-BMT can arise from a variety of origins and since the patients are highly immunosurpressed, rapid determination of the mechanisms underlying complications is highly desired.

Recently, investigators have transduced lymphocytes for delayed introduction with a single selectable marker, the gene, neomycin phosphotransferase (neo). Thereafter, PCR was employed to monitor the gene in cells biopsied from the patient. However, this method is cumbersome and PCR is time consuming (19). For example, prior to infusing the transduced markers into a patient, expression of neo must be verified. Expression of neo in transduced lymphocytes takes about two weeks time. During such time, the lymphocytes grown in culture often undergo self-tranformation and mutation of their original characteristics. Also, during such time, the recipient patient's clinical condition often changes for the worse.

Any vector carrinying a marker gene, to be useful in the present context is safe, efficient, and preferably must not substantially interfere with the lymphocyte's range of immune functions or its longevity (persistence) in the recipient's immune/circulatory system.

Hence, it is desired to provide a vector carrying a marker which permits efficient and fast expression, easy detection, by methods such as fluorescence activated cell sorting, easy monitoring after infusion (particularly of peripheral lymphocytes) and of course, is safe and nonimmunogenic. This would permit better, speedier, specific diagnosis of complications, and concommitantly, more successful treatment.

SUMMARY OF THE INVENTION

An overall objective of the invention is to provide a method useful for bone marrow transplant, that is, where it is desired to replace the hematopoeitic stem cells of a recipient patient with those of another. In particular, it is desired to make allogeneic bone marrow transplantation more efficacious, safer, and available to a larger number of patients. In particular, the present invention provides a method of treating or preventing complications associated with delayed introduction of T lymphocytes to a patient having previously received an allo-BMT depleted of T lymphocytes.

It is another object of the invention to provide a safe, efficient vector for transducing lymphocytes for delayed introduction to a patient having previously received an allo-BMT depleted of T lymphocytes. It is a further objective to provide a vector which does not interfere with the lymphocyte's functions and which will persist in the recipient's system. Such a vector contains at least (i) an easily selectable cell surface marker. Most preferably, the vector also contains (ii) a suicide gene, which can be activated in vivo to trigger cell death should a complication correlated with the transduced cells occur. In a most preferred embodiment, the vector contains only genes (i) and (ii).

It is yet another object of the invention to provide a simple, fast method of monitoring transduced donor lymphocytes according to the invention, after their introduction post allo-BMT. According to the invention, monitoring is performed by obtaining a biological sample suspected of containing transduced lymphocytes from the patient, and detecting the presence or absence of transduced lymphocytes by means of a cell surface marker. In a preferred embodiment, cells are monitored by using florescence activated cell sorting or magnetic sorting (immunobeads).

In another embodiment of the invention, it is possible to monitor and determine whether transduced donor lymphocytes introduced post-BMT are correlated causally to a complication(s) which arises after their introduction. According to this method, a biological sample is taken from the patient and tested to determine the presence of the marker. The results are correlated against the clinical symptoms of the complication. If a positive correlation is made, then the complication can be treated by specific elimination of the transduced cells. This elimination is achieved by use of a "suicide" gene, a negative selectable gene whose expression product renders the transduced cell susceptible (directly or indirectly) to cell death, by administration of a drug, for example.

It is another object of the invention to treat graft versus host disease which may develop with introduction of transduced lymphocytes into an allo-BMT patient. According to this method, the transduced lymphocytes are made sensitive to a particular agent or drug as a result of the expression of the negative selectable suicide gene. Therefore, by administering the appropriate agent/drug to the patient, virtually all of the transduced cells are killed.

It is another object of the invention to increase the therapeutic benefits of post-allo-BMT lymphocyte introduction, while simultaneously substantially eliminating the graft versus host disease side effect associated with lymphocyte introduction. Benefits provided by transduced donor lymphocytes according to the invention include an increased therapeutic graft-versus-leukemia response, antiviral response and disease prevention. The transduced lymphocytes according to the invention are fully alloreactive with leukemia, viruses and other pathogens.

In yet another object of the invention, a marker is provided for transduction of mammalian cells, in addition to human lymphocytes. In particular, a marker according to the invention can be used in connection with an exogenous gene for insertion into cells, as in the case of gene therapy, in order to monitor the presence of the exogenous gene. Most preferably, the marker and exogenous gene are in the same reading frame.

Further still, a marker and suicide gene system is provided for transduction of mammalian cells, in addition to human lymphocytes. In particular, a vector containing both a marker and suicide gene according to the invention can be used in connection with an exogenous gene for insertion into cells, as in the case of gene therapy. When employed together with an exogenous gene, the marker and suicide gene system permits a clinician or investigator to eliminate the expression of the exogenous gene in vivo, if desired. In a preferred embodiment, a vector is provided that carries the marker, exogenous gene and suicide gene in the same reading frame.

BRIEF DESCRIPTION OF THE DRAWINGS

FIG. 1(A). Schematic map of integrated SFCMM-2 proviral genome, indicating the HSVTK internal promotor (T). Solid boxes denote long-terminal repeat sequences. ΔLNGFR, modified form of the low-affinity receptor for nerve growth factor; TN, fusion gene encoding a bifunctional protein carrying both HSV-TK activity and (optionally) neomycin resistance. Arrows indicate transcription promoters.

FIG. 1(B). Ex vivo detection of transduced donor lymphocytes. FACS analysis for expression of ΔLNGFR on the cell surface and appropriate controls (Neg.) from peripheral blood (a and b) and bone marrow (c) samples of patient 1(a) and 8(b and c). The proportion of positive cells is indicated.

FIG. 1(D), (a) and (c). Polymerase chain reaction (PCR) analysis for the presence of the HSV-TK sequence on various samples from patient 8. (a) Lanes 3 to 6, peripheral blood samples obtained at monthly intervals beginning at day 3 from the second infusion (FIG. 3); lane 7, bone marrow sample obtained 23 days from infusion; lanes 1 and 2, negative controls; lanes 8 and 9, positive controls at two different levels of detection of positive cells ($10^{-4}$ and $10^{-3}$, respectively). (c) Lanes 1 and 3, two skin biopsy samples consistent for GvHD; lanes 2 and 5, negative controls; lane 4, positive control. (b) PCR analysis from patient 2. Lanes 3 to 6, peripheral blood samples obtained at monthly intervals beginning at day 4 from the second infusion (see FIG. 4); lanes 1 and 2, negative controls; lane 7, positive control.

FIG. 3. Clinical outcome in a patient affected by relapse of chronic myelomonocytic leukemia (CmML), following treatment by the infusion of transduced donor lymphocytes. Patient 8 underwent BMT from her HLA-identical MCL-compatible brother, but relapsed 3 months after transplant (as revealed by cytogenetic analysis, followed by a decrease in peripheral blood counts and marked morphologic myelodisplastic bone marrow). The patient received a total of $2 \times 10^7$ cells/kg donor lymphocytes. Marked cells could be easily detected by FACS analysis (FIG. 1(B)) and PCR (FIG. 1(D)) in the peripheral blood (reaching a peak at 11.9% of circulating mononuclear cells) and in bone marrow (reaching a peak at 5.3%). Infusions (arrows) were followed by a hematological reconstitution, as shown by the increase in the number of circulating leukocytes and platelets. Bone marrow cytogenetic analysis revealed a progressive decrease in the number of host hematopoietic cells (shaded area), and 100% donor engraftment (unshaded area) was observed after four infusions.

DETAILED DESCRIPTION OF PREFERRED EMBODIMENTS

I. The Vector System

In a first embodiment of the invention, a vector is provided which has exceptional properties useful in connection with transducing mammalian cells, particularly hematopoietic cells, for infusion into a human bone marrow transplant patient. In a preferred method, the vector is used to transduce lymphocytes. However, the vector's use is not limited to use in lymphocytes or the particular therapies described in the Examples, which describe transduced donor T-lymphocytes that are infused into a patient following an allo-BMT devoid of donor T-lymphocytes.

For example, a vector according to the invention is useful in connection with gene therapy, that is, inserting a desired exogenous gene into mammalian cells, e.g., pancreatic cells, liver cells, brain cells, muscle cells, egg, sperm, embryonic or fetal, etc,. In particular, the vector according to the invention provides at least a marker for monitoring the presence of the inserted exogenous gene in vivo or ex vivo.

More preferably, the vector employed in gene therapy can provide a marker and suicide gene system in order to permit elimination of cells transduced with the exogenous gene (i) in the event that the transduced cells cause complication(s) that outweigh the benefit of the presence of the transduced cells, or (ii) in the event it is desired to terminate the lives of the transduced cells in vivo.

Namely, the vector contains an easily selectable cell surface marker. According to the present invention, the vector preferably also contains a suicide gene, which can be activated in vivo to trigger cell death should a complication correlated with the transduced cells occur.

The cell surface marker according to the invention, is detectably labelled on the surface of the cell, for example by a labelled antibody or labelled ligand, and is preferably, but not limited to, a modified cell surface receptor. A cell surface marker according to the invention, is one that is not normally expressed on the surface of the mammalian cell to be transduced (and which is modified to eliminate signal transduction, as detailed below). To permit differentiation among transduced (marked) and unmarked blood cells, for example, a cell surface receptor can be chosen from a set of receptors that are expressed only in brain or spinal tissue (substantially not expressed on blood cells), such as forms of "trk" receptor, or non-immunogenic fetal receptors that are not normally expressed in fully developed humans. Similarly, to permit differentiation among transduced (marked) and unmarked cells of the central nervous system, a cell surface receptor can be chosen from a set of receptors that are expressed only in a type of non-CNS tissue, such as an hepatic-specific receptor (e.g. bile acid receptor proteins, LDL receptor, etc).

A preferred marker in this context is a human cell surface receptor molecule that is modified to eliminate the functional activity of the marker. Modification can be made, for example, by truncating the receptor, or otherwise mutating the portion of the molecule that performs signal transduction. A resultant modified receptor can no longer transduce a signal, yet retains its binding activity with respect to a cognate antibody or ligand.

Further, a cell surface receptor chosen according to the invention, when applied for use in humans, necessarily is expressed by normal human cells. By design, therefore, the modified cell surface receptor, when expressed in transduced human cells, is non-immunogenic.

A preferred vector according to the invention carries a first region that encodes a modified low affinity nerve growth factor receptor ("modified LNGFR" or "ΔLNGFR"). Modified LNGFR, when expressed on the surface of transduced cells retains the binding properties of the corresponding unmodified NGF receptor with respect to its ligand, yet cannot effect signal transduction as a result of ligand binding. Examples of specific LNGFR modifications are described in U.S. Ser. No. 08/602,791. According to the invention, modified LNGFR also is useful in many different types of gene therapies (for example, in treating ADA (adenosine deaminase disorder), CF (cystic fibrosis) and a variety of diseases being treated with gene therapy), with the possible exception of treatments specifically targeted to the CNS or brain, where the normal expression of LNGFR may make it problematic to differentiate marked from unmarked cells.

A vector according to the invention preferably carries both marker and a suicide gene, which, upon being transduced into a host cell, expresses a phenotype permitting negative selection (i.e., virtual elimination) of stable transductants. Examples of suicide genes can include HSV-TK, or cytosine deaminase, for example. Other possibilities include suicide genes described in International Application WO 92/08796, which is incorporated by reference herein in its entirety. Any suicide genes employed must be safely expressed and efficaciously negatively selected for in vivo. Preferably, the negative selectable phenotype confers a drug sensitivity. Drug sensitivity makes it possible to administer a drug in order to eliminate virtually all of the transduced cells. In a preferred embodiment, HSV-TK gene is used, which renders the transduced cells sensitive to the drug ganciclovir.

Figure 1A:
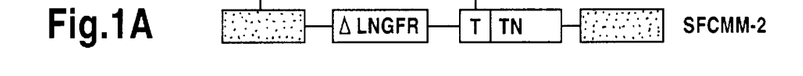

According to the invention, a vector is most preferably a retrovirus. Retroviruses have been shown to be useful in gene therapy and are advantageous in the present context for transducing lymphocytes because they infect primarily only dividing cells. The LTR-based vector is preferred for gene transfer and expression into human PBLs(13). The integrated SFCMM-2 proviral genome, shown in FIG. 1A (13, 14) was used successfully as a vector in the Examples set forth below.

In yet another novel aspect of the invention, the most preferred vector for allo-BMT is a modified version of SFCMM-2, "modified SFCMM-2" which carries only two genes: a first gene encoding ΔLNGFR, and a second (suicide) gene encoding HSV-TK protein. Specifically, modified SFCMM-2 carries, under control of the LTR, ΔLNGFR and HSV-TK, but it excludes the gene encoding for neomycin phophotransferase (neo). The inventors have now discovered that neo's expression in vivo in some patients, is immunogenic. Clinically, neo's immunogenicity is of course, detrimental, particularly for immunosupressed BMT patients.

Modified SCFMM-2 thus preferably carries only two genes, since concerns for safety and non-immunogenicity mitigate against inclusion of any additional genes beyond what is absolutely necessary for the vector to accomplish its purpose. In the instance when modified SCFMM-2 is utilized in gene therapy to introduce a desired exogenous gene for therapeutic purposes, the vector preferably carries only three genes (marker, suicide, and a desired exogenous gene)

A vector according to the present invention undergoes testing for safety and efficacy. The safety and efficacy of the SFCMM-2 vector were extensively tested in vitro and in vivo in small-animal models (15). The suicide gene, herpes simplex type I thymidine kinase (HSV-TK) gene, has been successfully transferred into various cell lines to confer ganciclovir sensitivity. Its efficacy has been demonstrated both in vitro and in vivo (10–12). The safety of modified SFCMM-2 is increased relative to SFCMM-2 It is envisioned that other suicide genes, other cell surface markers, or retroviruses may alternatively be used in the methods of the invention, provided they are shown to be similarly safe and efficacious.

In methods of treating allo-BMT according to the invention, the cells transduced by the vector (preferably modified SCFMM-2) are donor T-lymphocytes. "Donor" means that the cells are from the original donor of hematopoetic cells used in the allogeneic BMT. Hematopoietic cells also are transduced by a vector according to the invention.

In methods of gene therapy in which a vector according to the invention additionally carries an exogenous gene, a multitude of cell types may be transduced. For example, a desired exogenous gene can be inserted into modified SCFMM-2 using conventional genetic engineering techniques to provide a vector useful for transducing cells for gene therapy "GT-modified SCFMM-2". Depending on the type of gene therapy to be performed, the cell-type will vary. Examples of cell types which are transduced according to the invention preferably include cells which most readily lend themselves to ex vivo manipulation, i.e. red blood cells, B-lymphocytes.

It is further contemplated that, in methods of gene therapy according to the invention, other vectors in addition to retroviral vector, such as adenovirus-derived vector, are manipulated to carry the marker and suicide gene of the invention. For example, an adenoviral vector carrying LNGFR and the suicide gene HSV-TK is useful to transduce in vivo cells such as lung, bronchial and epithelial cells with a normal exogenous gene to treat bronchio-epithelial diseases (for example, cystic fibrosis). In methods of gene therapy, II. Selection and Monitoring of Transductants According to the invention, the use of a cell surface marker provides important advantages over conventional markers for gene therapy, that typically involve nuclear markers (e.g., the gene neo), identifiable only by nucleic acid detection methods such as PCR. In contrasts, a cell surface marker permits faster, easier detection ex vivo of cells expressing marker, for example, fluorescence-activated cell sorting (FACS) analysis (13). Cell surface markers (i.e., ΔLNGFR), allow rapid in vitro selection of transduced cells by the use of magnetic immunobeads conjugated to antibodies (i.e., anti-LNGFR antibody).

A biological sample from which the marker can be detected preferably is a set of peripheral blood lymphocytes, but can include biopsied material from the patient in any tissue of the body where the lymphoctyes would be expected, partiflularly for monitoring GvHD signs (for example, liver).

Importantly, the detection methods enabled by use of the present invention are quicker, and permit faster clinical assessment of the infused cells' performance. Additionally, in the initial transduction of cells to be infused, ΔLNGFR expresses much faster (1–2 days) than does neo (about 2 weeks). Lymphocytes kept in culture for prolonged lengths of time tend to change shape and diversify. Thus, the time savings gained from using cell surface receptor are beneficial in many ways (13).

In the clinical trials detailed in the Examples infra, after one round of gene transfer, 20 to 50% of donor lymphocytes were transduced. However, after one round of immunoselection, the proportion of transduced donor cells ranged between 95.0 and 99.6% (16). Immunoselection at the high rate of 95–99.6% selection offers time-saving benefits, as are mentioned immediately above. Also, prior to introducing the transduced lymphocytes in post-allo BMT treatment, immunoselection at this high proportion yields, in a single selection, a set of transduced donor lymphocytes to be infused in which virtually all carry the "suicide" gene (13). Clinically, it is critical for the infused donor lymphocytes to virtually all carry the suicide gene to ensure efficacious treatment of any GvHD which may develop. Thus, according to the invention, a single selection can be performed either on a set of transduced lymphocytes to be infused to yield, preferably at least 95% –100% transduced lymphocytes (PBLs).

Monitoring of infused transduced donor lymphocytes can be performed, preferably, by taking a sample of the recipient patient's peripheral blood (in preservative free heparin), and using FACS analysis to determine the frequency of cells expressing the surface marker gene and ex vivo characterization of the transduced cells. Confirmation of the presence of transduced donor cells at low frequency, such as in biopsied biological material, is performed by PCR and or reverse PCR.

III. Reconstituting Immunity, Guidelines for Dosage of Donor Lymphocytes

At the time of allo-BMT, recipient patients are severely immunodepressed. Normally, in a drug-induced immunosuppression, such as in organ transplant recipients, removal of pharmacologic immunosuppression will enable fast reconstitution of the immune system. This in not the case in post allo-BMT recipients. For this reason, the prognosis for recurrent viral infections (particularly Epstein Barr Virus) has been, up to now, dramatically severe.

According to the invention, a strategy is provided for reconstituting immunity in order to treat or prevent a complication in post-allo BMT recipients having previously received an allogenic donor bone marrow transplant that was depleted of lymphocytes. Reconstitution of immunity is achieved by introducing transduced donor lymphocytes after a delay following BMT in increasing dosages, as detailed in Example 2. In such a strategy, graft versus host disease can be avoided, while enhanced immunity can be achieved resulting in a therapeutic graft versus leukemia response, and sustained protection from viruses and disease.

The strategy to reconstitute immunity includes the following general regimen. First, transduced donor lymphocytes are prepared according to Example 1. The route of administration preferably is intravenous, although other routes into the circulatory system are contemplated. The lymphocyte preparation according to Example 1 is introduced into a suitable patient after delay following post allo-BMT in variable dosages, depending on the patient's general clinical status (what complications are being treated) as detailed below. (See Table 1 and Example 2). However, the following general guidelines apply to most patients, to begin at $10^5$ cells/Kg per body weight per day, until a total of $10^7$ cells/Kg is reached, according to the recipient's condition. Examples of dosages that were given in clinical trials are found in Example 2. General guidlines are offered immediately below.

(A) Prevention of Disease Relapse

For example, to prevent disease relapse, transduced donor lymphocytes can be infused every two weeks, beginning at day 30 after marrow reconstitution (ANC<500) at escalating cell doses, beginning at $10^5$ cells/Kg per body weight per day, until a total of $10^7$ cells/Kg is reached, or until relapse or GvHD occurs.

(b) Treatment of Disease Relapse

For example, to treat disease relapse, transduced donor lymphocytes can be infused every two weeks, beginning at day 30 after marrow reconstitution (ANC<500) at escalating cell doses, from about $10^5$ cells per Kg body weight per day until reaching a total of $10^8$ cells per Kg body weight per day, within about 8 weeks time from the beginning of treatment. Infusion of donor lymphocytes should be discontinued if GvHD grade II or higher occurs. (For treatment of CMV disease, treatment will first start by administering HD iv IfG and foscarnet, if appropriate).

(C) Treatment of Epstein-Barr Virus-Induced B Lymphoproliferative Disorders (EBV-BLPD)

For example, to treat EBV-BPLD, transduced donor lymphocytes can be infused at an initial dose of about $0.5 \times 10^6$ cells per Kg body weight per day to about $1.5 \times 10^6$ cells per Kg body weight per day. Infusion of donor lymphocytes is repeated weekly until complete remission is achieved or until GvHD grade II or higher occurs.

IV. Treating Leukemic Relapse and EBV-lymphoproliferative Disorders

In the past, leukemic relapse and Epstein Barr viral disorders have been treated by using antigen-specific lymphocytes. In contrast, treatment according to the invention with transduced donor T-lymphocytes provides fully-functional lymphocytes that are alloreactive when challenged with tumor or viral antigens. Therefore, the present invention eliminates the previous time consuming and difficult practice of developing antigen-specific lymphocytes to treat leukemia and viral pathogens. The clinical regimen for treating leukemic relapse and for treating EBV is described in Example 2; however, more preferably, the clinical regimen employs modified SCFMM-2 instead of the SCFMM-2, described below.

EBV is a human herpes virus that normally replicates in epithelial cells of oropharyngeal tract, and it is able to immortalize B lymphocytes in vitro (17). As with other herpes virus, reinfection with EBV is probably mainly due to a reactivation of latent virus. In BMT recipients, the primary event in the pathological cascade is uncontrolled proliferation of mature B lymphocytes. EBV reactivation may arise from residual host B cells, blood transfusion, or oropharyngeal epitheleal cell shedding. The transformed B cells have an immunoblastoid or plasmocytoid appearance (17), express virus encoded latent cycle nuclear antigens, and are positive for most latent membrane proteins. In addition, they express a number of cell adhesion molecules. All these phenotypic features would make them intensely vulnerable to the immune system of a normal individual.

In the normal host, in fact, EBV-induced lymphoid proliferation is controlled by EBV specific and MHC-restricted T-lymphocytes able to be cytotoxic toward EBV transformed cells (18, 19), by MHC-unrestricted cytotoxic T-lymphocytes (20), and by antibodies directed toward specific viral antigens. The profound immunosuppressive state of a transplanted patient allows uncontrolled proliferation of EBV-transformed cells. Usually, a lymphoma pattern with lymphoadenopathy and hepatosplenomegaly is observed. However, the proliferative lymphoblasts may infiltrate a variety of organs including lung, liver, kidney, gut, and bone marrow. The B cell proliferation may be polyclonal in the early stages, but eventually becomes oligoclonal or monoclonal.

Initial reactivation of EBV with the features of an infectious mononucleosis like illness may resolve, but once frank lymphoproliferation has developed, the course is rapidly progressive. Since a limited number of specific cytotoxic T lymphocytes is required for controlling EBV-transformed B lymphocytes in normal individuals, the administration of donor lymphocytes for the occurence of BLPD in recipients of T-lymphocyte depleted BMT could control this severe complication by providing to the patient donor immunity against EBV.

V. Treatment of Graft Versus Host Disease

If, in monitoring the patient or the patient's transduced donor lymphocytes after infusion, it is found that they are alloreactive with the recipient patient's own cells, then those lymphocytes can be negatively selected for in vivo (by activation of the suicide gene) to relieve the complication. If the patient begins to exhibit symptoms of graft versus host disease concurrent with, or within a few days, weeks or months after infusion of the transduced donor lymphocytes, then steps are taken to determine whether a GvHD complication positively correlates with the transduced lymphocytes. For example, bilirubin levels are detected, and these values are correlated with the timing and presence of transduced lymphocyte in the circulating peripheral blood lymphocytes. Additionally, liver biopsy may be performed and liver cells analyzed immunohistochemically and by PCR for presence of transduced donor lymphocytes in affected liver cells.

Upon positively correlating the complication or graft versus host disease state with the donor transduced lymphocytes, an investigator may administer a drug to trigger action of the suicide gene to kill the transduced cells.

In the instant Examples, wherein lymphocytes were transduced with SFCMM-2 vector, patients were treated with ganciclovir at 10 mg/Kg/day when patient(s) exhibited at least Grade II, or Grade III or higher. Daily infusions of ganciclovir can continue as indicated until GvHD symptoms regress; however, preferably only a few days, or less than 5 days of daily administration is necessary.

The clinical regimen for GvHD is described in Example 2. More preferably, the clinical regimen employs modified SCFMM-2 instead of SCFMM-2.

EXAMPLES

Example 1

Preparation of Donor Lymphocytes for Infusion

Peripheral blood mononuclear cells (PBMCs) were collected from the BMT donor by leukapheresis and separated from the red cells and neutrophils by Ficoll-Hypaque density-gradient centrifugation. The PBMCs were then washed, counted, and cultured at $\sim 2 \times 10^6$ cells per 2 milliliter well in 24-well tissue culture plates containing RPMI 1640 with 5% human serum in the presence of recombinant human interleukin-2 (IL-2) (Euro-Cetus Italy S.r.I., Milan, Italy).

1. A Transduction with SCFMM-2

For gene transfer, donor T-lymphocytes were cocultured with irradiated packaging cell line for more than 48 hours in the presence of Polybrene (8 $\mu$g/ml), beginning the first day of polyclonal stimulation with phytohemagglutinin (2 $\mu$g/ml). No modification of culture conditions was introduced until the end of the procedure. (F. Mavilio et al., Blood 83, 1988 (1994); and Bordignon and C. Bonini, Hum. Gene. Ther. 6, 813 (1995); incorporated by reference in there entireties). After gene transfer via SCFMM-2, transduced cells were selected for the expression of the cell surface marker ΔLNGFR by means of specific immunobeads. Cells were incubated with the murine monoclonal antibody 20.4 to human ΔLNGFR (American Type Culture Collection). After 30 minutes cells were washed and incubated with immunomagnetic beads coupled to a rat antibody to mouse immunoglobulin G1. After 45 minutes, positive cells were separated by use of magnetic immunobeads and incubated overnight at 37° C. to remove antibody-coated beads. After one round of selection, the proportion of transduced cells was assessed by cytofluorimetric analysis (13). Up to this point of the study, a second round of selection was never required to achieve the indicated levels of purity. Cells were then cryopreserved for future infusions.

In vitro ganciclovir sensitivity of HSV-TK-transduced lymphocytes (15), as well as acyclovir resistance (10), were confirmed, as has been described previously. Before clinical use, cells were required to meet the specifications already in use in other clinical human gene therapy experiments. In particular, cells were tested for replication-competent retroviruses, IL-2-independent growth, and for adventitious infectious agents.

Figure 2A:
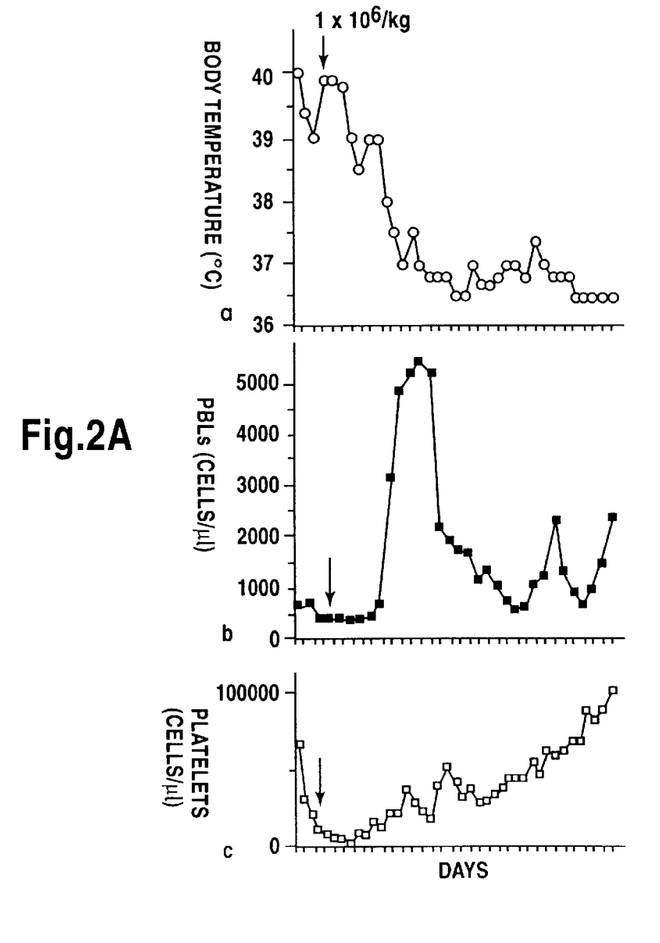
FIG. 2(A). Graphs (a to c) show clinical outcome of patient affected by Epstein-Barr virus-induced B lymphoproliferative disorders (EBV-BLPD), when treated with transduced donor lymphocyte infusion (detailed in Example 2B). Hematological reconstitution occurred, as shown by an increase in the number of circulating platelets FIG. 2A(c).

Transduced donor cells were infused by intravenous injection in saline with 4% human serum albumin at the time of diagnosis of complication (Table 1) and subsequently at least at monthly intervals (14). In some patients (FIGS. 2 and 4) the schedule was adjusted in accord with clinical status and nature of the complication. Preferably, each infusion of donor lymphocytes is preceded by a premedication with clorpheniramin 10 mg iv.

Example 2

Clinical Trials beginning at $10^5$ cells/Kg per body weight per day, until a total of $10^7$ cells/Kg is reached, beginning at $10^5$ cells/Kg per body weight per day, until a total of $10^7$ cells/Kg is reached, beginning at $10^5$ cells/Kg per body weight per day, until a total of $10^7$ cells/Kg is reached, Eight patients were treated by infusion of transduced donor lymphocytes post-allo- BMT, as reported in Table 1, below.

Table 1

Clinical characteristics of the eight patients described in Example 2. Disease status was assessed through examination of marrow aspirates and biopsy, cytogenetic examination, and molecular analysis. EBV-BLPD was determined by serologic data and histologic evaluation as indicated. Exclusion criteria for the infusion of transduced donor lymphocytes included the presence of a GvHD grade II or higher and CMV reactivation requiring ganciclovir treatment. This study was approved by the Institutional Ethical Committee (14, 31), and all patients gave informed consent. NHL, non-Hodgkin lymphoma; CML, chronic myeloid leukemia; AML, acute myeloid leukemia; CmML, chronic myelomonocytic leukemia; EBV-BLPD, Epstein-Barr virus-induced B lymphoproliferative disorder; CR, complete remission; PR, partial response; NR, no response; NE, not evaluable.

were infused at an initial dose of $1\times10^6$ cells/kg, a higher initial dose, as was necessitated by the rapid progression of this complication and suggested by the previous clinical study (6).) No toxicity or complication that could be related to the gene transfer procedure (17) was observed in this study, whose results are reported below.

2 B. Treatment of EBV-BLPD

The successful clinical regression of EBV-BLPD in Patient 1 after transduced donor lymphocyte infusions is shown in FIG. 2. Patient 1 underwent a BMT from her HLA-identical and MLC-compatible brother for a high-grade lymphoma in second remission. After successful engraftment, the patient developed EBV-BLPD confirmed by morphological examination of a laterocervical node biopsy and by in situ hybridization for EBV RNA in the nuclei of the neoplastic cells. A myeloaspirate and a bone marrow biopsy showed overt infiltration of the bone marrow by lymphoid paratrabecolar nodules causing marrow failure.

Figure 2B:
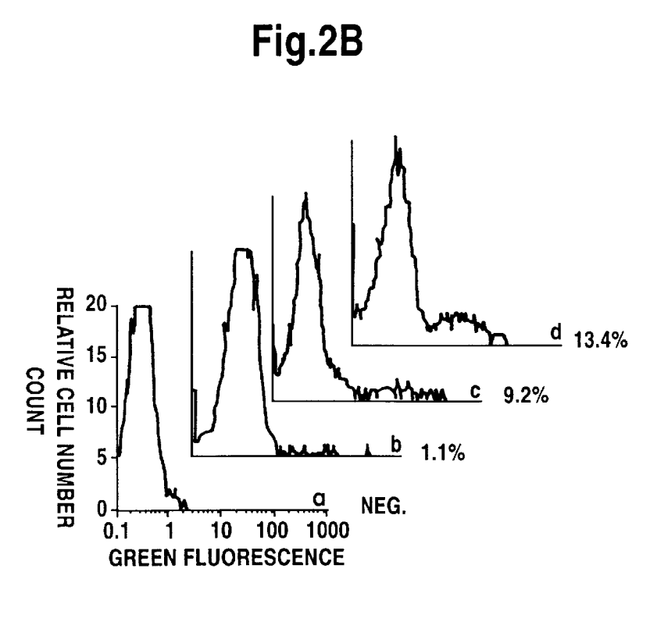
FIG. 2(B). Proportion of marked donor cells in peripheral blood (b to d), and negative control (a).

The patient received a total dose of $1.5\times10^6$ cells/kg (6) of transduced donor lymphocytes. In the 2 weeks after administration of donor cells (arrow), all clinical symptoms associated with EBV-induced B cell proliferation regressed as shown by body temperature decrease (FIG. 2A(a)). At the time of regression of clinical symptoms, a sharp increase in PBL counts was observed, shown in FIG. 2A(b). Circulating transduced donor lymphocytes were almost exclusively $CD3^+CD8^+$ lymphocytes (>90% of total mononuclear cells from day +10 to day +15), with high proliferation index. Meanwhile, a hematological reconstitution occurred, shown by an increase in the number of circulating platelets FIG. 2A(c). During this time, marked donor cells increased progressively in the patient's peripheral blood up to 13.4% of total mononuclear cells, as shown in FIG. 2B(b to d). The three blood samples were obtained at day 3, 10, and 20 after infusion, and the proportion of positive cells is indicated. FIG. 2(B) shows the negative control.

Example 2C

Further Results From Clinical Trials of Patients Listed in Table 1

(1) Antigen-Specific Response Exhibited by Transduced Donor Lymphocytes

Persistence of antigen-specific responses were observed. In the patient treated for an EBV-induced lymphoma, transduced cells were detected that exhibited EBV-specific activ-

| Patient | Disease | Complication (weeks after BMT) | First infusion (weeks after complication | No. of lymphocytes infused (× $10^6$ cells/kg) | Clinical outcome |
|---|---|---|---|---|---|
| 1 | NHL | EBV-BLPD (+7) | 2 | 1.5 | CR |
| 2 | CML | CML relapse (+28) | 11 | 38.6 | PR |
| 3 | CML | CML relapse (+84) | 192* | 4.5 | PR |
| 4 | AML | AML relapse (+45) | 1 | 3.3 | NR |
| 5 | AML | AML relapse (+14) | 1 | 4.9 | NR |
| 6 | CML | EBV-BLPD (+5) | 1 | 0.5 | NE |
| 7 | AML | AML relapse (+24) | 2 | 11.1 | CR |
| 8 (+19) | CmML | CmML relapse | 4 | 20.5 | CR |

*Patient 3 received idrossiurea and interferon-α before the infusion of transduced donor cells.

2 A. Treatment of Leukemic Relapse

For the treatment of leukemic relapse, (patients 2–5, 7 and 8), SFCMM-2-transduced donor lymphocytes were infused at increasing cell doses, beginning at $10^5$ cells per kilogram of body weight to a total of $4\times10^7$ cells/kg. (For the treatment of EBV-BLPD, transduced donor lymphocytes ity for the first time after administration of donor cells. The frequency of EBV-specific cells was ~1:1000, as compared to the frequency of 1:1300 that was detected in the donor PBLs before and after ex vivo vector transduction. This level was achieved after administration of a small dose of donor cells (FIG. 2 and Table 1).

After administration of ganciclovir to treat GvHD, specific reactivity of the transduced donor cells in the peripheral blood of the patient was monitored and detected at the reduced frequency of 1:3250. No linear correlation was observed between the number of infused transduced donor lymphocytes and persistence or detection. Rather, the intensity of antigen response and proliferation of donor cells seemed to affect levels of detection. In particular, patient 1 reached the level of 13.4% positivity after a total injection of only $10^6$ cells/kg to treat EBV-BLPD. Patient 8, who achieved similar levels of positivity (11.9%), did so after receiving an order of magnitude higher infusion of cells to treat chronic myelomonocytic leukemia (CmML) relapse. Other patients who received even higher cell doses did not reach similar levels of positivity. As expected, viral antigens were able to induce a more rapid and intense specific proliferation of transduced cells than leukemic cells (19).

(2) Detection of Persistent Transduced Donor Lymphocytes Among Circulating Lymphocytes and Biopsied Tissues Extensive manipulation of the cells that undergo ex vivo gene transfer by retroviral vectors could potentially modify their immune repertoire and their activation status, thus affecting their in vivo survival and function. In all but one of the 8 reported patients who received transduced donor lymphocytes, genetically modified cells could be repeatedly detected in the circulation, in marrow aspirates, and in tissue biopsies.

Small amounts of peripheral blood in preservative-free heparin were obtained immediately before and after each lymphocyte infusion, weekly for the first 3 months after infusion, and monthly for the remainder of the first year and were used for the following immunological and gene marking studies: (i) cytofluorimetric analysis for the frequency of cells expressing the cell surface marker gene and for the ex vivo characterization of transduced cells; (ii) confirmation of the presence of transduced donor lymphocytes by PCR; (iii) G418 selection for detection and expansion of neo-transduced cells; (iv) ex vivo analysis of the persistence of ganciclovir sensitivity; and (v) ex vivo detection of immunity against transduced donor lymphocytes by standard mixed lymphocyte culture and cytotoxic assays (25). Any diagnostic biopsy, including biopsies performed to detect GvHD, were used for the following studies: (i) immunohistochemical assays for the expression of the cell surface marker in infiltrating lymphocytes; (ii) analysis for vector gene presence by PCR; and (iii) immunophenotype of infiltrating lymphocytes. Serum, plasma, cells and biopsies collected at specific time points were frozen for future analysis. After the administration of ganciclovir, peripheral blood samples were obtained daily for the first week and weekly thereafter. The in vivo selective elimination of transduced donor lymphocytes was monitored by means of the same immunological and gene marking criteria reported above.

Figure 1B:
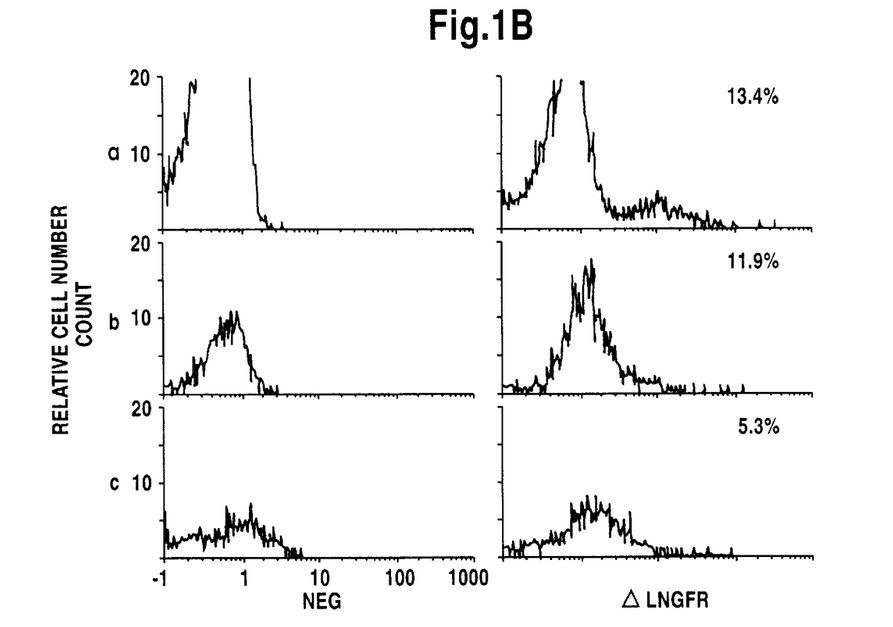
Figure 1C:
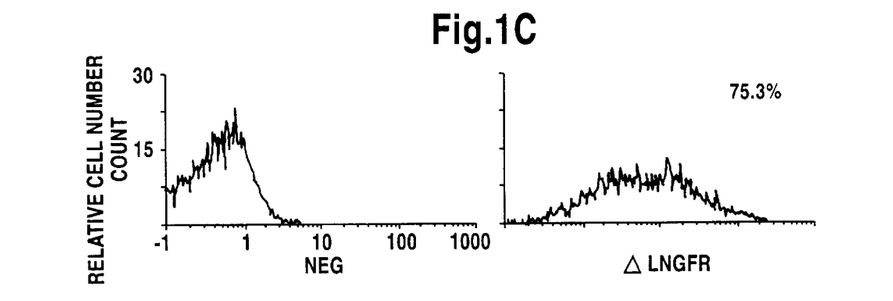
FIG. 1(C). Fluoresence activated cell sorting (FACS) analysis for expression of ΔLNGFR on lymphocytes obtained after G418 selection of peripheral blood lymphocytes (PBLs) from patient 2 and the appropriate control. The proportion of positive cells reported, 75.3%, is derived from comparison with the negative control and is underestimated because analysis of the sample revealed the presence of a cell population that homogeneously expressed the cell surface marker. On the x axis of (B) and (C), it is labeled as the logarithmic scale of green fluorescence.

In circulating lymphocytes, the proportion of transduced donor cells ranged between the level of detection by polymerase chain reaction (PCR) ($10^{-4}$) and 13.4% (FIG. 1B). At various times of follow-up, some patients had only low frequencies of circulating transduced cells, below the level of detection in FACS analysis. In these cases, ex vivo-transduced donor cells were selected by culture in the presence of G418 (a neomycin analog), and selected cells homogeneously expressed the cell surface marker (FIG. 1C).

Figure 1D:
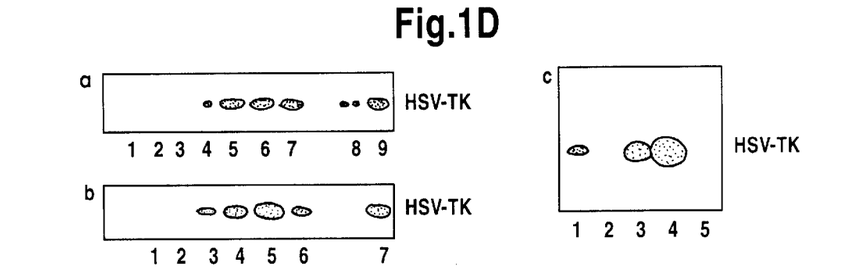

Additionally, the presence of transduced donor lymphocytes in PBLs, BM samples, and GvHD lesion sites was confirmed by PCR analysis and was followed over time (FIG. 1D). Persistent transduced cells were detected for more than 12 months after the last infusion of transduced donor cells. Persistence of antigen-specific responses also was observed.

(3) Immunological Activity of Transduced Donor Lymphocytes In Vivo.

Figure 3:
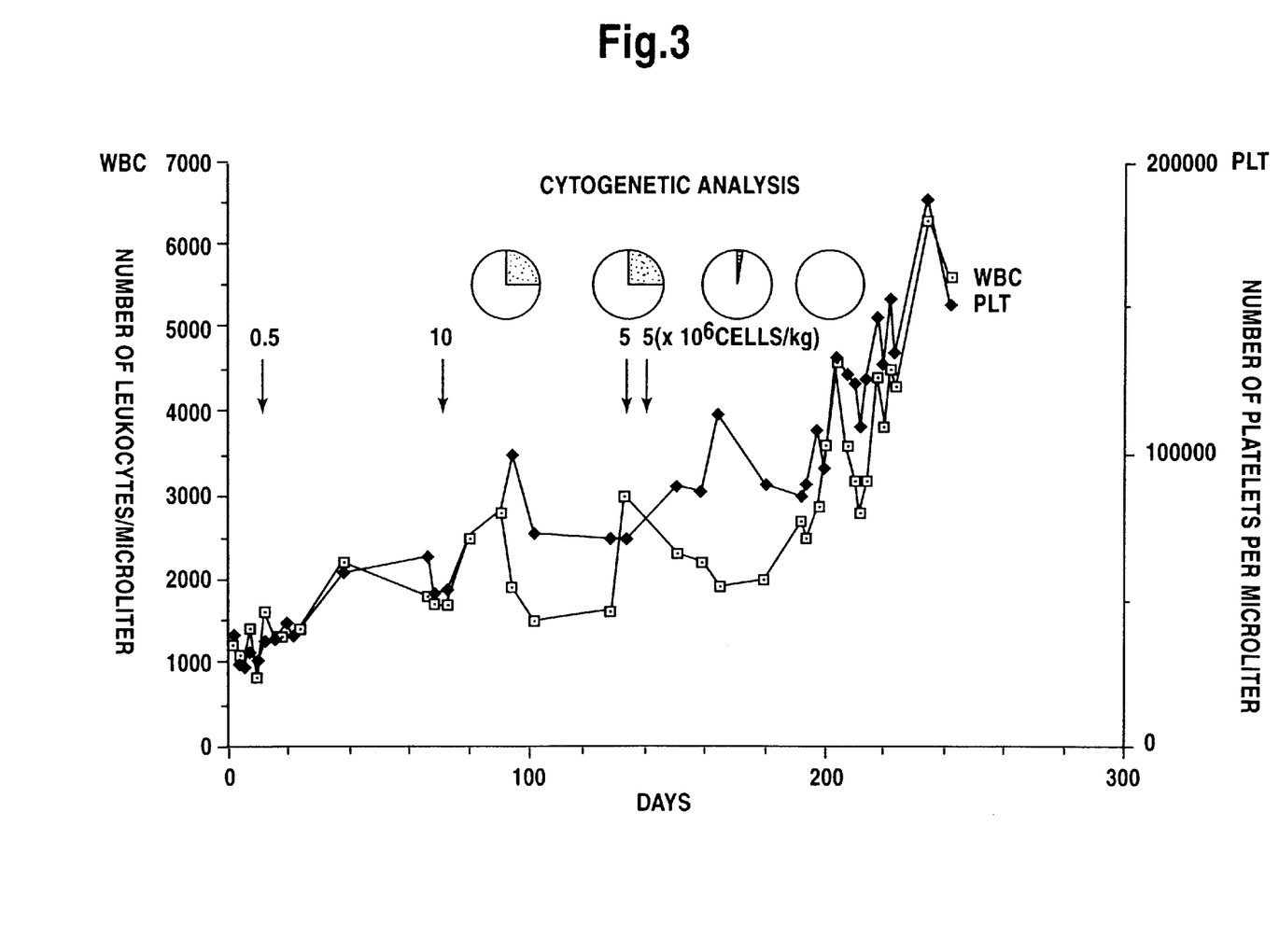

The in vivo function of genetically modified donor lymphocytes was revealed by antitumor responses, immune reconstitution, and alloreactivity. Patients were monitored weekly for the first month and monthly thereafter for detailed clinical history, complete physical examination including skin examination for the presence of GvHD), and general laboratory evaluation [including complete blood count and differential, urinalysis, blood urea nitrogen creatinine, bilirubin, aspartate transaminase (AST), alanine transferase (ALT), alkaline phosphatase, Na, K, Cl, albumin, total protein, glucose, and radiographic evaluation] as indicated. Disease status was assessed through examination of marrow aspirates and biopsy, cytogenetic analysis, and molecular analysis In five out of the eight patients in this series, therapeutic graft verus leukemia (GvL) response was detected, with three complete responses (Table 1). Three patients developed GvHD. The patients who achieved full remission included patient 1, treated for an aggressive EBV-induced lymphoma, and patient 8, treated for leukemic relapse (FIGS. 2 and 3). These results were obtained in the absence of any chemotherapeutic agent. A third patient (patient 7, Table 1) achieved full remission after administration of genetically modified donor lymphocytes and chemotherapy. Patient 3 relapsed twice after two subsequent allogenic BMTs for CML and could be maintained in CML chronic phase for over 5 years. During this period, all donor cells disappeared from the marrow and the circulation. After the long interval in chronic phase, the CML progressed to accelerated phase and was treated by the infusion of transduced donor lymphocytes (total dose, $4.5 \times 10^6$ cells/kg). This was followed by conversion to chronic phase and by the reappearance of donor chimerism, as monitored by the progressive conversion of the blood type from B to the donor type A (21). In this patient, the increase of the donor blood type erythrocytes closely followed the appearance of circulating transduced donor lymphocytes.

Thus, the procedures associated with ex vivo gene transfer of the marking and therapeutic genes by the SFCMM-2 vector preserved the in vivo potential of allogeneic PBLs and their antigen-specific reactivity. Additionally, this observation was further confirmed in a small series of patients in which genetically modified and unmodified donor PBLs were used. In a patient with moderate skin GvHD, it was possible to determine by immunostaining and PCR that both cell populations positive and negative for the cell surface marker ΔLNGFR were contributing to the lymphocyte infiltrate present in the lesion (22).

Example 2D

Treatment of GvHD

Table 2 shows the effect of ganciclovir treatment on elimination of transduced donor lymphocytes, and on GvHD.

Table 2

The effect of ganciclovir treatment on elimination of transduced donor lymphocytes, and on GvHD.

| Patient | GvHD (grade) | Pre-ganciclovir | Proportion of ALNGFR + PBLs (%) 24 hours after ganciclover | Clinical outcome |
|---|---|---|---|---|
| 1 | Acute skin (II/III) | 13.4 | $<10^{-4}$ | CR* |
| −2 | Acute liver (III) | 2.0 | $<10^{-4}$ | CR† |
| 8 | Chronic (extended) lung, skin, G.I. | 11.9 | 2.8 | PR‡ |

*Complete remission was revealed by clinical observation of complete regression of all skin GvHD signs.
†Complete remission was revealed by the disappearance of all physical and biochemical signs of liver GvHD (FIG. 4 and text).
‡Partial remission of the severe obstructive bronchiolitis was revealed by physical evaluation and spirometric analysis. Amelioration of skin GvHD, but not of oral mucosa, was also observed. In oral mucosa, persistence of chronic GvHD and of genetically modified cells was confirmed histologically and by PCR, respectively. In patient 1 and 2, given the complete elimination of clinical signs of a GvHD, a biopsy immediately after ganciclovir treatment was considered inappropriate and was not performed later as part of the patients' monitoring were consistently negative for the presence of the transgene (PCR) and for GvHD.

Two patients in this series developed acute GVHD and were treated with ganciclovir. If grade II GVHD or higher occurred, patients who had previously received transduced donor lymphocytes were treated with ganciclovir (10 mg/kg per day) for 7 days or less if all the GvHD signs and symptoms regressed. Patients who had previously received inclusions of both transduced and untransduced donor lymphocytes were initially treated with ganciclovir at 10 mg/kg per day, to down-regulate GvHD.

Figure 4:
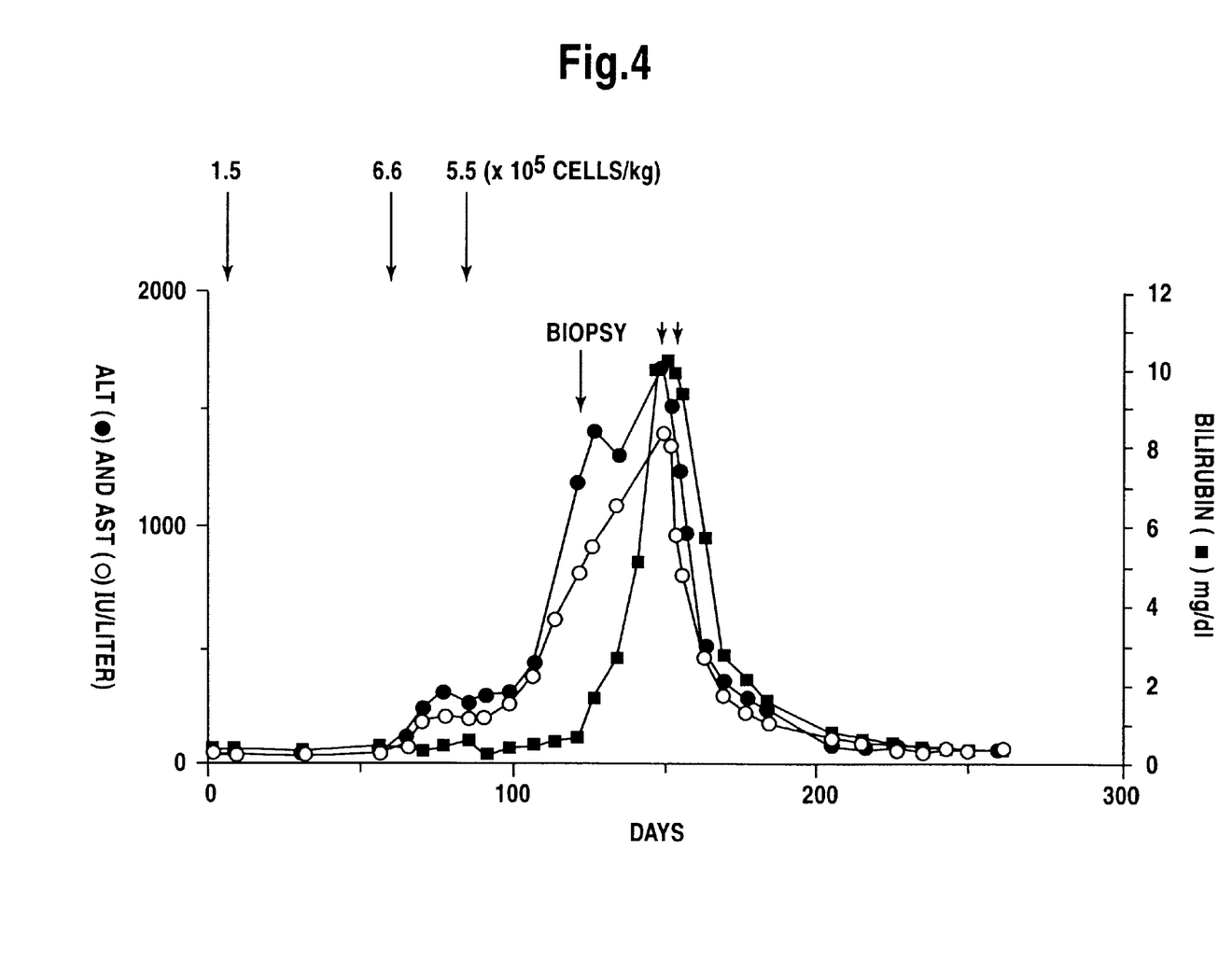
FIG. 4. Values of bilirubin and liver function enzymes in patient 2, who developed acute GvHD after the infusion of transduced donor lymphocytes. Long arrows, infusions of transduced donor cells; shorter arrow, timing of the liver biopsy performed to detect acute GvHD (biopsy). The double arrow head indicates the period of the four infusions of ganciclovir (10 mg/kg per day).

Patient 2 relapsed 6 months after allo-BMT and was treated by increasing doses of transduced donor cells. Marked cells could be detected in the peripheral blood by FACS analysis and PCR. After the third infusion of transduced donor lymphocytes (total of $1\times10^6$ cells/kg), values of the patient's bilirubin and liver function enzymes rapidly increased (FIG. 4). A liver biopsy revealed acute GvHD, and the patient was treated with ganciclovir (10 mg/kg per day). All transduced donor lymphocytes and all GvHD clinical and biochemical signs then disappeared (FIG. 4 and Table 2), in the absence of any local or systemic toxicity. Elimination of transduced donor cells preceded normalization of liver enzymes with similarly sharp kinetics (FIG. 4 and Table 2). Indeed, after 1 day of treatment, genetically modified cells decreased below the level of PCR detection ($10_{-4}$) and remained below this level until a second infusion of transduced cells was administered 21 days later. Because no immunosuppressive drug was administered to this patient, the complete abrogation of the severe liver GvHD could be attributed exclusively to the expression of the TK transgene.

Four weeks after the infusion of donor lymphocytes, patient 1 progressively developed signs of acute GvHD, confirmed by a skin biopsy. The intravenous administration of two doses of ganciclovir (10 mg/kg) resulted in progressive rapid reduction from 13.4% to below PCR detection (Table 2). The treatment was followed by the disappearance of clinical signs of skin GvHD. About 3 weeks after infusions of HSV-TK-transduced cells, patient 8 presented chronic GvHD involving skin, oral mucosa, and lungs. Immunohistochemical analysis and PCR revealed the presence of genetically modified cells in the biopsy. This patient was then treated with ganciclovir (10 mg/kg per day) for 7 days, resulting in improvement of clinical conditions and a decrease of GvHD signs. The correlated reduction in the proportion of circulating transduced donor cells to 2.8% was achieved in the first 24 hours (Table 2). Complete elimination of genetically modified donor lymphocytes could not be obtained despite extended treatment.

Although fluctuations in the numbers of circulating transduced lymphocytes were observed at various times of follow-up, reduction of circulating transduced donor lymphocytes comparable to that described in these three patients was never observed in any of the patients in the study in the absence of ganciclovir treatment. This is best compared to the lack of any spontaneous remissions of a grade II or higher of GvHD in the 258 patients treated with donor lymphocytes in the EBMT (European Bone Marrow Transplantation) international collaborative study (24).

The two treated patients who had achieved full remission before ganciclovir administration remained in full remission after elimination of donor lymphocytes by ganciclovir. Thus, the transfer of the HSV-TK gene by the SFCMM-2 vector may provide a tool for in vivo modulation of alloreactivity and effective and specific treatment of acute GvHD in the absence of any immunosuppressive drug.

2D (a) Lack of Toxicity Associated with Ganciclovir Administration

As anticipated, no local or systemic toxicity was observed that could be related to the gene transfer procedure or to ganciclovir administration. No significant modifications of the total counts of leukocytes, PBLs, natural killer cells, or other T cell subsets could be detected in patients who had received ganciclovir treatment for GvHD. This confirms that lymphocytes do not produce the in vivo bystander effect observed in other cell types (10, 12). The only unwanted effect observed in this study was a specific immune response to HSV-TK-NEO in one patient who had received genetically modified cells late after transplant, after return to immunocompetence (25). The immune response was expressed only to the HSV-TK-NEO fusion protein. No immunity to the cell surface marker ΔLNGFR was detected in any patient (25).

2D (b) Conclusions from GVHD Treatments

In this context, the transfer of a suicide gene for selective and specific elimination of effector cells of GvHD provides a new tool to combine the benefits of allo-PBLs with the possibility of eliminating GvHD without toxic effects. The extensive manipulation of the cells that undergo ex vivo gene transfer gave rise to a concern that the transduced donor PBLs may not provide a therapeutic clinical outcome as compared to unmodified counterparts. That is, there was concern that manipulation may reduce the allogeneic advantage, or even exacerbation of GvHD. The fact the transduced PBLs exhibited both long-term survival (29) and immunocompetence confirmed the usefulness of this treatment. Further, the functioning of the transduced PBLs in mechanisms underlying GvHD, GvL, and antiviral responses are likely to be different and to involve different effector cells. The long term preservation of an intact immune repertoire, and the full range of functions observed in the transduced PBLs further confirmed the benefit of this strategy.

Optimal effects achieved likely were attributable to the rapid positive selection of system for transduced cells allowed by the cell surface marker (13). Ganciclovir-mediated elimination of HSV-TK-transduced cells was efficacious in the presence of acute GvHD. In only one case of chronic GvHD was ganciclovir treatment not fully effective. Transduced cells isolated ex vivo from this patient showed unmodified sensitivity to ganciclovir, suggesting that in vivo resistance could indeed be due to the activation state of the genetically modified lymphocytes. This is supported by the well-known cell replication-dependent activity of HSV-TK (30). If confirmed in extended clinical studies, these results will expand the number of candidate patients benefiting from T lymphocyte-depleted allo-BMT, by allowing the use of less-compatible marrow donors.

REFERENCES

The references listed below are hereby incorporated by reference in their entireties.
1. E. D. Thomas et al., Ann. Intern. Med. 104, 155 (1986).
2. R. O'Reilly, Curr. Opin. Hematol. 1, 221 (1993).
3. M. M. Horowitz et al., Blood 75, 555 (1990).
4. N. A. Kernan et al., ibid. 74, 2227 (1989); J. M. Goldman et al., Ann. Intern. Med. 108, 806 (1988).
5. H. J. Kolb et al., Blood 76, 2462 (1990); J. Szer, A. P. Grigg, G. L. Phillips, W. P. Sheridan, Bone Marrow Transplant. 11, 109 (1993); D. L. Porter, M. S. Roth, C. McGarigle, J. L. M. Ferrara, J. H. Antin, N. Engi. J. Med. 330, 100 (1994); F. Van Rhee et al., Blood 83, 3377 (1994); S. Makinnon et al., ibid. 86, 1261 (1995); S. Slavin et al., ibid. 87, 2195 (1996); W. R. Drobyski et al., ibid. 82, 2310 (1993); G. Tricot et al., ibid. 87, 1196 (1996).
6. E. B. Papadopoulos et al., N. Engl. J. Med. 330, 1185 (1994).
7. C. M. Rooney et al., Lancet 345, 9 (1995).
8. S. R. Riddell et al., Science 257, 238 (1992); E. A. Walter et al., N. Engl. J. Med. 333, 1038 (1995).
9. H. J. Kolb et al., Blood 86, 2041 (1995).
10. P. Tiberghien et al., ibid. 84, 1333 (1994).
11. F. L. Moolten et al., Hum. Gene Ther. 1, 125 (1990); F. L. Moolten et al., Cancer Gene Ther. 6, 279 (1994).
12. K. W. Culver and J. Van Gilder, Hum. Gene Ther. 5, 343 (1994).
13. F. Mavilio et al., Blood 83, 1988 (1994).
14. C. Bordignon and C. Bonini, Hum. Gene. Ther. 6, 813 (1995).
15. S. Verzeletti et al., in preparation.
16. See Example 1
17. WHO Handbook for reporting result of cancer treatment (WHO offset publication no. 48, 1979).
18. See Example 2C(2).
19. H. E. Heslop et al., Nature Med. 2, 551 (1996).
20. See Example 2C(3).
21. C. Bonini and S. Rossini, data not shown.
22. M. Ponzoni and L. Ruggieri, data not shown.
23. See Example 2D
24. H. J. Kolb, personal communication.
25. C. Traversari et al., in preparation.
26. G. B. Vogelsang and A. D. Hess, Blood 84, 2061 (1994); L. M. Faber, S. A. van Luxemburg Heijs, W. F. Veenhof, R. Willemze, J. H. Falkenburg, ibid. 86, 2821 (1995).
27. S. A. Giralt and R. E. Champlin, ibid. 84, 3603 (1994).
28. H. Waldman, S. Cobbold, G. Hale, Curr. Opin. Immunol. 6, 777 (1994).
29. T. Friedmann, Science 244, 1275 (1989); K. W. Culver, W. F. Anderson, R. M. Blaese, Hum. Gen. Ther. 2, 107 (1991); G. Ferrari et al., Science 251, 1363 (1991); W. F. Anderson, ibid. 256, 808 (1992); R. C. Mulligan, ibid. 260, 926 (1993); C. Bordignon et al., ibid. 270, 470 (1995); E. Marshall, ibid. p. 1751.
30. Y. C. Cheng et al., Proc. Natl. Acad. Sci. U.S.A. 80, 2767 (1983).
31. P. d. C. d. M. Comitato Nazionale per la Bioetica, Dipartimento per l'informazione e l'editoria (Societá e Istituzione publisher, 1991), pp. 1–48.

What is claimed is:

1. A vector for transducing cells, said vector having a nucleic acid comprising:

a) a first region encoding a modified low affinity nerve growth factor receptor (modified LNGFR), wherein said receptor is modified such that when expressed on the surface of cells transduced with said vector, the modified LNGFR retains the binding properties of the corresponding unmodified NGF receptor with respect to its ligand and acts as a marker, yet the modified LNGFR cannot effect signal transduction as a result of said ligand binding, b) a second region encoding a protein capable of conferring a negative selectable phenotype on cells transduced with said vector, operably linked to said first region.

2. A vector according to claim 1, wherein said second region of said nucleic acid comprises a gene that confers said negative selectable phenotype of drug sensitivity to cells transduced with said vector, which, upon administration of said drug to said cells, is toxic to most all of said cells.

3. A vector according to claim 2, wherein said second region of said nucleic acid comprises a HSV-TK gene that makes cells sensitive to ganciclovir upon the administration of ganciclovir to the cells.

4. An isolated, implantable human cell transduced with a vector according to claim 1.

5. A cell according to claim 4, wherein the second region of said nucleic acid comprises a HSV-TK gene.

6. A cell according to claim 4, wherein said cell is a T-lymphocyte.

* * * * *